(12) United States Patent
Mak

(10) Patent No.: US 10,970,661 B2
(45) Date of Patent: Apr. 6, 2021

(54) SYSTEM AND METHOD FOR MONITORING MOTION AND ORIENTATION PATTERNS ASSOCIATED TO PHYSICAL ACTIVITIES OF USERS

(71) Applicant: RaceFit International Company Limited, Hong Kong (HK)

(72) Inventor: Kwan Hang Mak, Hong Kong (HK)

(73) Assignee: Racefit International Company Limited, Hong Kong (HK)

( * ) Notice: Subject to any disclaimer, the term of this patent is extended or adjusted under 35 U.S.C. 154(b) by 456 days.

(21) Appl. No.: 15/398,749

(22) Filed: Jan. 5, 2017

(65) Prior Publication Data

US 2017/0197111 A1 Jul. 13, 2017

Related U.S. Application Data

(60) Provisional application No. 62/277,458, filed on Jan. 11, 2016.

(51) Int. Cl.
*G06Q 10/06* (2012.01)
*A61B 5/00* (2006.01)
(Continued)

(52) U.S. Cl.
CPC ...... *G06Q 10/06313* (2013.01); *A61B 5/1114* (2013.01); *A61B 5/1116* (2013.01);
(Continued)

(58) Field of Classification Search
CPC ... A61B 5/1123; A61B 5/7246; A61B 5/1114; A61B 2562/0219; A61B 5/1116;
(Continued)

(56) References Cited

U.S. PATENT DOCUMENTS

2006/0025282 A1  2/2006  Redmann
2009/0210078 A1*  8/2009  Crowley ............... G06Q 30/02
                                                              700/91
(Continued)

FOREIGN PATENT DOCUMENTS

CN     103282907 A    9/2013
CN     104305986 A    1/2015
CN     105050563 A    11/2015

OTHER PUBLICATIONS

Search Report of counterpart Hong Kong Short-term Patent Application No. 17100310.4 dated Feb. 10, 2017.
(Continued)

*Primary Examiner* — Jerry-Daryl Fletcher

(57) ABSTRACT

A system and method for monitoring motion and orientation patterns associated to physical activities of a user is disclosed. Data associated to a physical activity executed by a user is captured from one or more sensors. The data is compared with a plurality of pre-defined motion patterns in order to identify a matched motion pattern. Each pre-defined motion pattern further comprises a first reference threshold value and a second reference threshold value indicating the successful execution of the physical activity. A first threshold value and a second threshold value pertaining to the physical activity executed by the user is determined. The first threshold value and the second threshold value is compared with a first reference threshold value and a second reference threshold value, respectively, corresponding to the matched motion pattern. Finally, an output indicative of the performance of the user in executing the physical activity is notified to the user.

17 Claims, 8 Drawing Sheets

(51) Int. Cl.
 *A61B 5/11* (2006.01)
 *G09B 19/00* (2006.01)

(52) U.S. Cl.
 CPC .......... *A61B 5/1121* (2013.01); *A61B 5/1124* (2013.01); *A61B 5/6804* (2013.01); *A61B 5/7246* (2013.01); *G09B 19/0038* (2013.01); *A61B 5/0022* (2013.01); *A61B 5/681* (2013.01); *A61B 5/6803* (2013.01); *A61B 5/6823* (2013.01); *A61B 5/6824* (2013.01); *A61B 5/6828* (2013.01); *A61B 5/6898* (2013.01); *A61B 5/7264* (2013.01); *A61B 5/7282* (2013.01); *A61B 2503/10* (2013.01); *A61B 2562/0219* (2013.01); *A61B 2562/0223* (2013.01)

(58) Field of Classification Search
 CPC .............. A61B 5/7282; A63B 24/0062; A63B 2024/0068; A63B 24/0006; G06F 3/017; G09B 19/0038; G09B 19/003
 See application file for complete search history.

(56) References Cited

U.S. PATENT DOCUMENTS

| | | | |
|---|---|---|---|
| 2013/0053990 A1* | 2/2013 | Ackland | G06Q 30/02 700/91 |
| 2013/0063432 A1* | 3/2013 | Kaps | G06T 13/40 345/419 |
| 2013/0158686 A1* | 6/2013 | Zhang | G01C 22/006 700/91 |
| 2014/0270375 A1 | 9/2014 | Canavan et al. | |
| 2015/0019135 A1 | 1/2015 | Kacyvenski et al. | |
| 2015/0201867 A1 | 7/2015 | Peindl et al. | |
| 2016/0058372 A1* | 3/2016 | Raghuram | A61B 5/0205 600/595 |

OTHER PUBLICATIONS

Search Report issued by the Chinese Patent Office dated Apr. 29, 2016.
International Search Report of PCT Patent Application No. PCT/CN2017/070491 dated Apr. 12, 2017.

* cited by examiner

SYSTEM AND METHOD FOR MONITORING MOTION AND ORIENTATION PATTERNS ASSOCIATED TO PHYSICAL ACTIVITIES OF USERS

CROSS-REFERENCE TO RELATED APPLICATIONS AND PRIORITY

The present application claims priority from U.S. provisional application No. 62/277,458, filed on Jan. 11, 2016, the entirety of which is incorporated herein by reference.

TECHNICAL FIELD

The present subject matter described herein, in general, relates to monitoring physical activities of a user, and more particularly to a system and method for monitoring motion and orientation patterns associated to the physical activities of a user.

BACKGROUND

In the recent times, with the use of inertial measuring unit (IMU), digital coaching wearable products are becoming popular in the market. By combining the data captured from accelerometer(s), gyroscope(s), and magnetometer, the IMU may detect motion and orientation in three-dimensional space. The motion and orientation information may enable in determining the performance of the users in execution of various physical activities related to sports and/or exercises thereby recommending an appropriate training and/or coaching devices to the users.

However, since the users are of varying body shapes/sizes and having varied skill levels in differential physical activities, the existing systems face a technical problem of accurately/effectively discerning the posture of the users thereby failing to appropriately determine accurate performance of the users in executing the physical activities.

SUMMARY

This summary is provided to introduce the concepts related to a system and a method for monitoring motion and orientation patterns associated to physical activities of users and the concepts are further described in the detail description. This summary is not intended to identify essential features of the claimed subject matter nor is it intended to use in determining or limiting the scope of claimed subject matter.

In one implementation, a system for monitoring motion and orientation patterns associated to one or more physical activities of a user is disclosed. The system may comprise one or more sensors, a processor in communication with the one or more sensors and a memory coupled with the processor. The processor may execute programmed instructions stored in the memory. The processor may execute a programmed instruction for capturing data associated to one or more physical activities executed by a user from one or more sensors, wherein the data comprises at least motion and orientation data. Further, the processor may execute a programmed instruction for comparing the data with a plurality of pre-defined motion patterns in order to identify a matched motion pattern, wherein each pre-defined motion pattern comprises a first reference threshold value and a second reference threshold value. In one aspect, the first reference threshold value and the second reference threshold value may indicate a baseline level and a minimum passing level, respectively, required for the successful execution of the one or more physical activities. The processor may further execute a programmed instruction for determining, based upon the data, a first threshold value and a second threshold value pertaining to the one or more physical activities executed by the user. The processor may further execute a programmed instruction for comparing the first threshold value and the second threshold value with the first reference threshold value and the second reference threshold value, respectively, corresponding to the matched motion pattern. Furthermore, the processor may execute a programmed instruction for notifying an output to the user based upon the comparison, wherein the output is indicative of the performance of the user in executing the one or more physical activities.

In another implementation, a method for monitoring motion and orientation patterns associated to one or more physical activities of a user is disclosed. The method may comprise capturing, by a processor, data associated to one or more physical activities executed by a user from one or more sensors, wherein the data comprises at least motion and orientation data. Further, the method may comprise comparing, by the processor, the data with a plurality of pre-defined motion patterns in order to identify a matched motion pattern, wherein each pre-defined motion pattern comprises a first reference threshold value and a second reference threshold value. In one aspect, the first reference threshold value and the second reference threshold value may indicate a baseline level and a minimum passing level, respectively, required for the successful execution of the one or more physical activities. The method may further comprise determining, by the processor, based upon the data, a first threshold value and a second threshold value pertaining to the one or more physical activities executed by the user. The method may further comprise comparing, by the processor, the first threshold value and the second threshold value with the first reference threshold value and the second reference threshold value, respectively, corresponding to the matched motion pattern. Furthermore, the method may comprise notifying, by the processor, an output to the user based upon the comparison, wherein the output is indicative of the performance of the user in executing the one or more physical activities.

In yet another implementation, a non-transitory computer readable medium storing program for monitoring motion and orientation patterns associated to one or more physical activities of a user is disclosed. The program may comprise a programmed instruction for capturing data associated to one or more physical activities executed by a user from one or more sensors, wherein the data comprises at least motion and orientation data. Further, the program may comprise a programmed instruction for comparing the data with a plurality of pre-defined motion patterns in order to identify a matched motion pattern, wherein each pre-defined motion pattern comprises a first reference threshold value and a second reference threshold value. In one aspect, the first reference threshold value and the second reference threshold value may indicate a baseline level and a minimum passing level, respectively, required for the successful execution of the one or more physical activities. The program may further comprise a programmed instruction for determining, based upon the data, a first threshold value and a second threshold value pertaining to the one or more physical activities executed by the user. Further, the program may comprise a programmed instruction for comparing the first threshold value and the second threshold value with the first reference threshold value and the second reference threshold value, respectively, corresponding to the matched motion pattern. Furthermore, the program may comprise a programmed instruction for notifying an output to the user based upon the comparison, wherein the output is indicative of the performance of the user in executing the one or more physical activities.

BRIEF DESCRIPTION OF DRAWINGS

The detailed description is described with reference to the accompanying Figures. In the Figures, the left-most digit(s) of a reference number identifies the Figure in which the reference number first appears. The same numbers are used throughout the drawings to refer like features and components.

DETAILED DESCRIPTION

Figure 1:
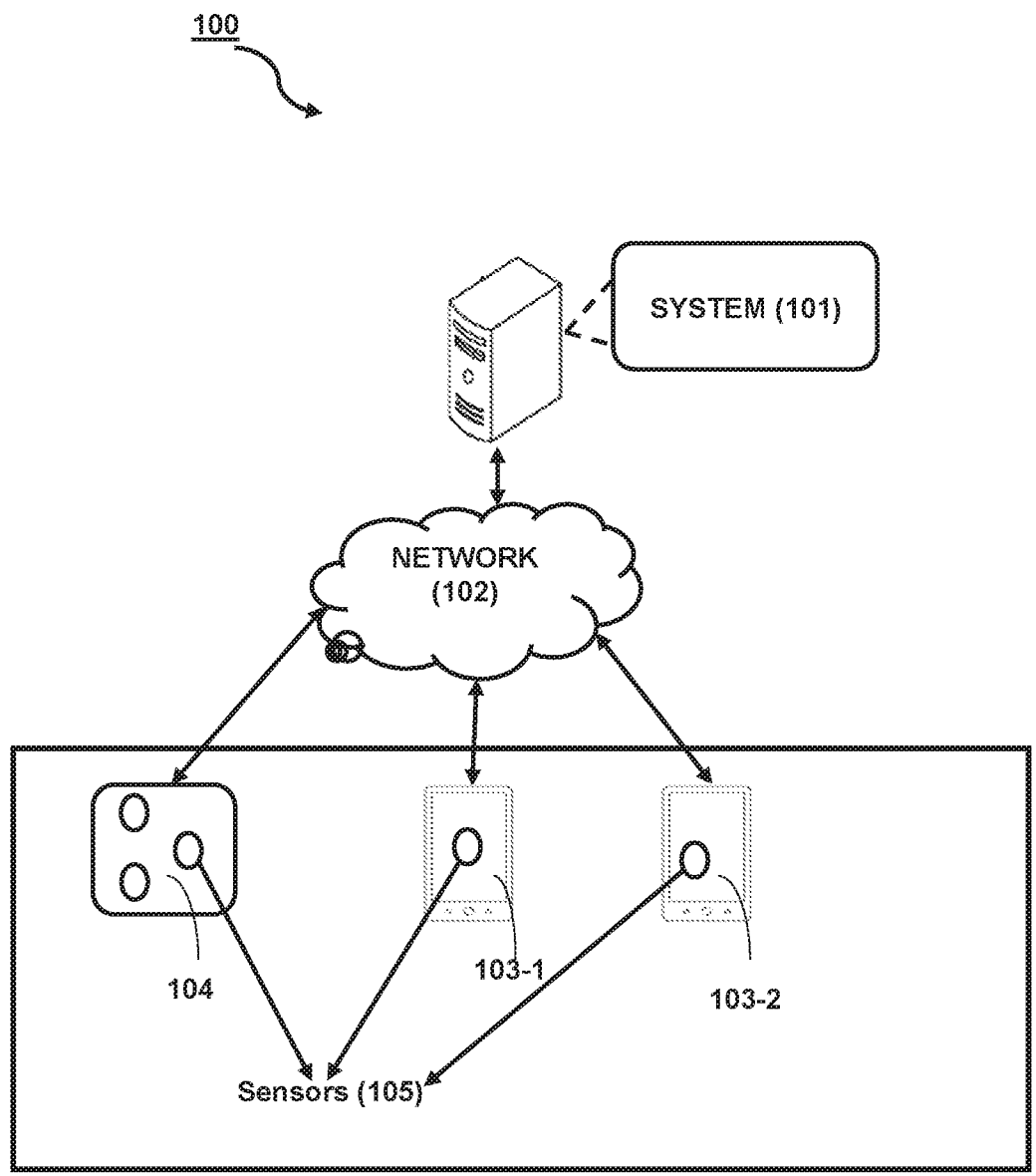
FIG. 1 illustrates a network implementation 100 of a system 101 for monitoring motion and orientation patterns associated to one or more physical activities of a user, in accordance with an embodiment of the present application.

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments.

System(s) and method(s) for monitoring motion and orientation patterns associated to one or more physical activities of a user are described herein. In one aspect, each of the one or more physical activities may be related to a physical exercise and/or a sport. One or more sensors may be deployed in order to sense motion and orientation data (hereinafter referred as "sensor data" or "data" interchangeably) associated to the one or more physical activities executed by the user. In one example, the one or more sensors may be Inertial measurement unit (IMU) sensors (e.g. accelerometer, gyroscope, and magnetometer etc.) present within a handheld device (e.g. a smartphone) of the user or a wearable device (e.g. a smart garment, a smart glass and a smartwatch etc.) associated with the user. Further, the sensor data captured via the one or more sensors may be at least one of a tilting angle, a curvature angle, an extension angle, a flexion angle and a combination thereof. The sensor data captured may be stored within the handheld device or the one or more sensors or a server (e.g. a cloud server) communicatively coupled with the handheld device.

In one aspect, the sensor data may be compared with a plurality of predefined motion patterns in order identify a matched pattern corresponding to the sensor data associated to the one or more physical activities executed by the user. In one aspect, each pre-defined motion pattern comprises a first reference threshold value and a second reference threshold value. It must be understood that the first reference threshold value and the second reference threshold value may indicate a baseline level and a minimum passing level, respectively, required for the successful execution of the one or more physical activities. It is to be noted that the baseline level and the minimum passing level for each physical activity may be predefined based upon analysis of historical sensor data captured pertaining to a plurality of users.

In one aspect of the present application, a first threshold value and a second threshold value pertaining to the one or more physical activities executed by the user may be determined based upon the sensor data. Specifically, the sensor data may be processed to determine the first threshold value corresponding to the first reference threshold value and the second threshold value corresponding to the second reference threshold value. Further, the first threshold value and the second threshold value may be compared with the first reference threshold value and the second reference threshold value, respectively, corresponding to the matched motion pattern. It is to be noted that the comparison of the first threshold value with the first reference threshold value and the of the second threshold value with the second reference threshold value is done in order to verify whether or not the motion pattern of the user while executing the one or more physical activities meets the baseline level and the minimum passing level required for the successful or correct execution of the one or more activities.

In one aspect, based upon the comparison result, the user may be notified with an output (e.g. audio/visual/text alert), wherein the output is indicative of user's performance in the execution of the one or more activities. In one example, a textual message "RIGHT/CORRECT" or "WRONG/INCORRECT" may be indicated as the output on the handheld device based upon successful or failure of the execution of the one or more physical activities.

In some embodiments, in order to monitor the motion and orientation patterns of the one or more physical activities of the user, a fuzzification technique may be implemented. In the fuzzification technique, the sensor data captured may be converted into fuzzified data using a predefined knowledge base. The knowledge base may comprise a plurality of rules indicating the performance results of the physical activities being performed, wherein the plurality of rules is derived based on historical data and expert information received from multiple experts in the physical activities of respective sports and/or exercises. In one example, the knowledge base may comprise a rule derived based on expert information received from a sport coach, wherein the rule indicates whether or not a particular motion and/or orientation associated to a particular sport is performed correctly by the user. The rules may be linked with respect to the sensor data captured via sensors in order to determine whether or not the activities being performed by the users is correct/incorrect based upon analysis of the sensor data and the rules. Therefore, the knowledge base may comprise a predefined mapping of the fuzzified data with historical data captured from the one or more sensors, wherein the historical data is associated to a plurality of users categorized into a plurality of groups. The plurality of users is categorized into the plurality of groups based upon age, Body-Mass Index (BMI), physical ability, location and a combination thereof.

In one aspect, the knowledge base may comprise one or more parameters enabling the conversion of the actual sensor data into the fuzzified data. In one example, the fuzzified data may have a value within a range of 0-1. The one or more parameters may be derived/generated based upon analysis of the historical data. In one example, the one or more parameters may comprise a group category, a type of physical activity, an intensity level of the physical activity being executed by the user, and the like. The knowledge base may comprise multiple fuzzified rules that may convert any sensor data into the fuzzified data based upon the one or more parameters as described above.

In one aspect, the knowledge base may further comprise a predefined mapping of the fuzzified data to a predefined output, the said predefined output indicating the performance of the users in executing the one or more physical activities. In one example, the mapping may indicate, based upon the fuzzified data, whether or not the user has executed the one or more physical activities correctly. The knowledge base may adaptively learn the probable output indicative of the performance based on the fuzzified data corresponding to the actual sensor data.

In another aspect, the output indicating the performance of the users in the one or more activities may be determined based upon a plurality of factors comprising weighting factor of the one or more sensors, the fuzzified data corresponding to the data captured by the one or more sensors and a coefficient (also referred hereinafter as "comprehensive coefficient" interchangeably throughout the present application). The weighting factor and the comprehensive coefficient are derived based upon analysis of the historical data within the knowledge base. The weighting factor may be derived based upon at least a location of the one or more sensors and a type of a physical activity being executed by the users.

It must be understood that the knowledge base may be frequently updated after a predefined time interval. Further, the updating of the knowledge base may comprise updating of the one or more parameters enabling the conversion of the data into the fuzzified data, the predefined mapping of the fuzzified data to a predefined output, the weighting factor of the one or more sensors and the comprehensive coefficient.

While aspects of system and method for monitoring motion and orientation patterns associated to one or more physical activities of a user may be implemented in any number of different computing systems, environments, and/or configurations, the embodiments are described in the context of the following exemplary system.

Referring to FIG. 1, a network implementation 100 of a system 101 for monitoring motion and orientation patterns associated to one or more physical activities of a user is illustrated, in accordance with an embodiment of the present application. Although the present application is explained considering that the system 101 is implemented as a server, it may be understood that the system 101 may also be implemented in a variety of computing systems, such as a laptop computer, a desktop computer, a notebook, a handheld device, a mobile device, a workstation, a mainframe computer, a network server, and the like. In one implementation, the system 101 may be implemented in a cloud-based environment.

Figure 2:
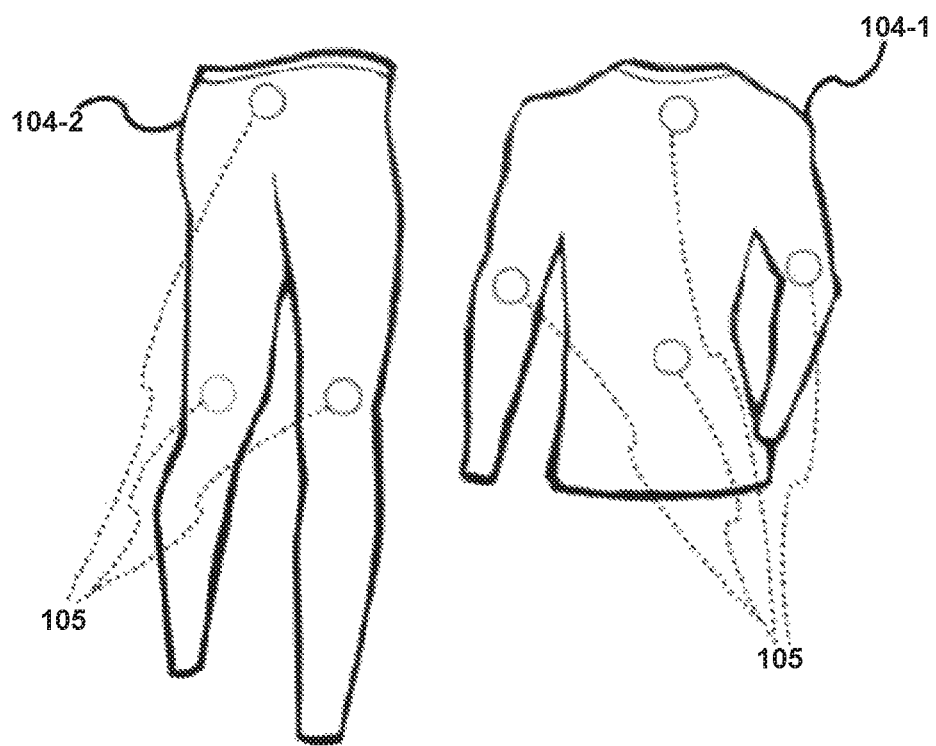
FIG. 2 illustrates motion sensing wearable devices (104-1, 104-2) comprising one or more sensors 105, in accordance with an embodiment of the present application.

It will be understood that the system 101 may be accessed by multiple users through one or more user devices 103-1, 103-2, 103-3 . . . 103-N, collectively also referred to as user devices 103 hereinafter, or applications (APPs) residing on the user devices 103. Examples of the user devices 103 may include, but are not limited to, a portable computer, a personal digital assistant, a handheld device, a workstation and the like. Further, the system 101 may be directly accessed by a wearable device 104 or the wearable device may access the system 101 through the user devices 103. Examples of the wearable device 104 may include a smart garment, a smart watch, a smart glass, a smart shoe, a necklace, and the like. The user devices 103 and the wearable device 104 may further comprise one or more sensors 105 (hereinafter referred as sensors 105). Examples of the sensors 105 may comprise an accelerometer, gyroscope, magnetometer, and the like. In one embodiment, the wearable device 104 may be an upper garment 104-1 and a lower garment 104-2 comprising inbuilt sensors 105 as shown in FIG. 2. The user devices 103 and the wearable device 104 are communicatively coupled to the system 101 through a network 102.

In one implementation, the network 102 may be a wireless network, a wired network or a combination thereof. The network 102 can be implemented as one of the different types of networks, cellular communication network (such as 2G/3G/4G etc.), local area network (LAN), wide area network (WAN), the internet, and the like. The network 102 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 102 may include a variety of network devices, including routers, bridges, servers, computing devices, storage devices, and the like.

Figure 3:
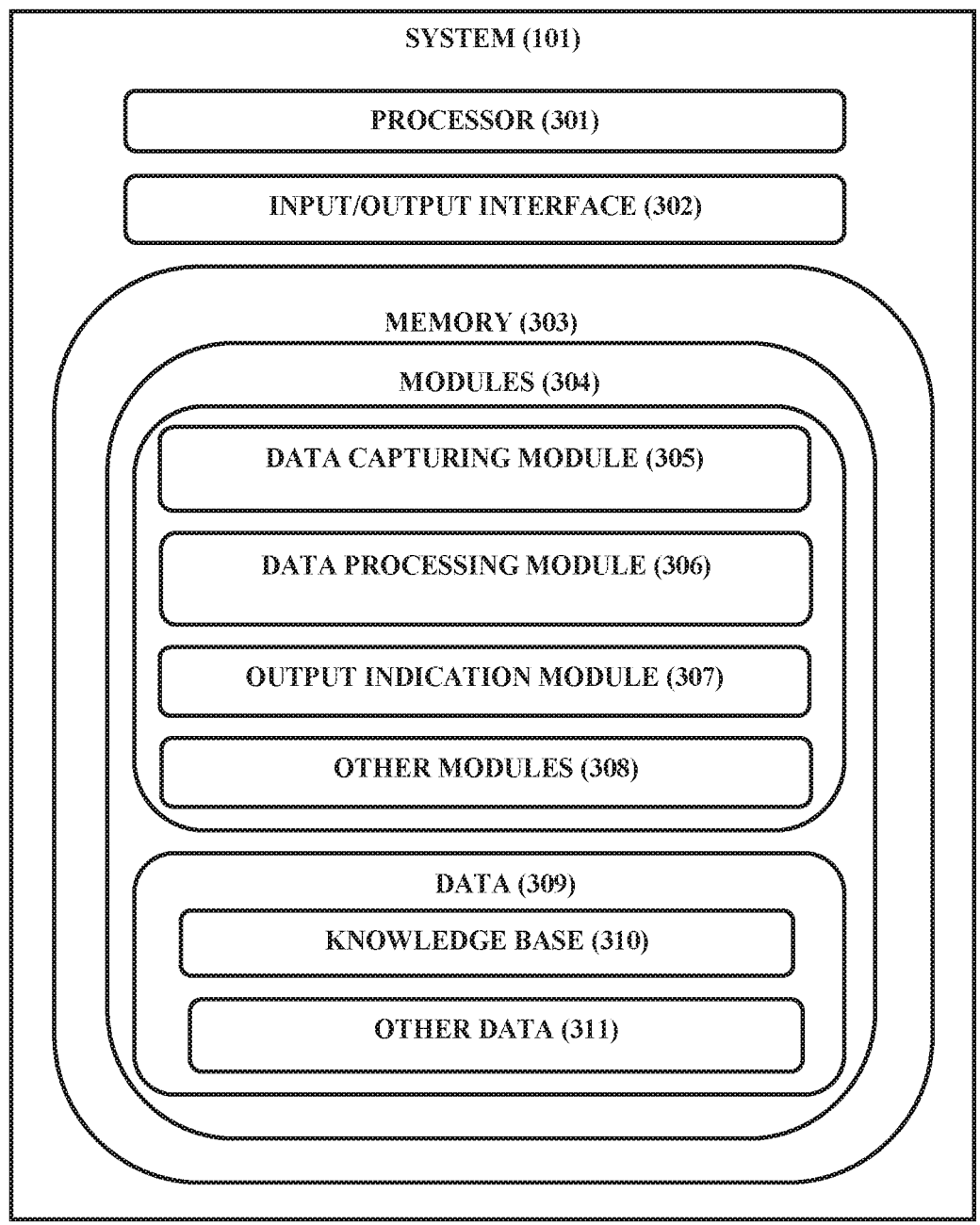
FIG. 3 illustrates the system 101 along with multiple components of the said system 101, in accordance with an embodiment of the present application.

Referring now to FIG. 3, the system 101 is illustrated in accordance with an embodiment of the present application. In one embodiment, the system 101 may include a processor 301, an input/output (I/O) interface 302, and a memory 303. The processor 301 may be implemented as one or more microprocessors, microcomputers, microcontrollers, digital signal processors, central processing units, state machines, logic circuitries, and/or any devices that manipulate signals based on operational instructions. Among other capabilities, the processor 301 is configured to fetch and execute computer-readable/programmed instructions stored in the memory 303.

The I/O interface 302 may include a variety of software and hardware interfaces, for example, a web interface, a graphical user interface, and the like. The I/O interface 302 may allow the system 101 to interact with a user directly or through the user devices 103. Further, the I/O interface 302 may enable the system 101 to communicate with other computing devices, such as web servers and external data servers (not shown). The I/O interface 302 can facilitate multiple communications within a wide variety of networks and protocol types, including wired networks, for example, LAN, cable, etc., and wireless networks, such as WLAN, cellular, or satellite. The I/O interface 302 may include one or more ports for connecting several devices to one another or to another server.

The memory 303 may include any computer-readable medium known in the art including, for example, volatile memory, such as static random access memory (SRAM) and dynamic random access memory (DRAM), and/or nonvolatile memory, such as read only memory (ROM), erasable programmable ROM, flash memories, hard disks, optical disks, and memory cards. The memory 303 may include modules 304 and data 309.

In one embodiment, the modules 304 include routines, programs, objects, components, data structures, etc., which perform particular tasks, functions or implement particular abstract data types. In one implementation, the modules 304 may include a data capturing module 305, a data processing module 306, an output indication module 307 and other modules 308.

The data 309, amongst other things, serves as a repository for storing data processed, received, and generated by one or more of the modules 304. The data 309 may also include a Knowledge base 310 and other data 311. The other data 311 may include data generated as a result of the execution of one or more modules in the other modules 308.

In one implementation, at first, a user may use the user device 103 to access the system 101 via the I/O interface 302. The user may register himself using the I/O interface 302 in order to use the system 101. The detailed working of the system 101 for monitoring motion and orientation patterns associated to one or more physical activities of a user using the plurality of modules 304 is explained referring to FIGS. 1-7 as below.

Referring to FIG. 1, the user, via the user device 103, may select a physical activity such as an exercise or a sport to be performed/executed by the user. In response to the user selection, the system 101, via the user device 103, may instruct the user to initiate the execution of the physical activity. The user may further, via the user device 103, instruct the sensors 105 located within the user device 103 or the wearable device 104 to sense data associated to the physical activity being executed/performed by the user. The sensors 105 may comprise IMU sensors enabling the capturing the sensor data as IMU information. The IMU information at least comprises a motion and orientation data associated with the physical activity being performed/executed by the user. In one example, the motion and orientation data include a tilting angle, a curvature angle, an extension angle, a flexion angle, and the like. The data capturing module 305 (as shown in FIG. 3) may capture the sensor data and thereafter store the sensor data in the data 309 for future reference and analysis.

Now referring to FIG. 3, the data processing module 306 may process the sensor data in order to analyze the motion and orientation data associated to the physical activity executed by the user. Firstly, the data processing module 306 may compare the sensor data with a plurality of predefined motion patterns stored in the data 309 in order to identify a matched motion pattern corresponding to the physical activity being executed by the user. It must be understood that each predefined motion patterns further comprise a first reference threshold value and a second reference threshold value indicative of a baseline value and a minimum passing level, respectively, required to be met for the successful/correct executing of the respective physical activities.

Figure 4A:
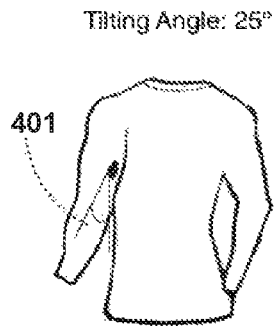
FIGS. 4a-4h illustrate various positions of the one or more physical activities executed by the user, in accordance with an embodiment of the present application.
Figure 4B:
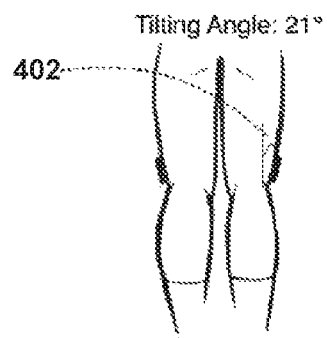
Figure 4C:
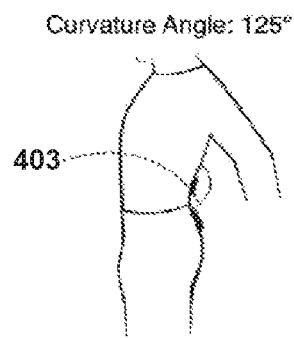

It must be noted that the baseline level and the passing level pertaining to each activity may be determined based upon static and dynamic calibration techniques implemented by the data processing module 306 pertaining to different physical activities performed by different users. In the static calibration technique, the data processing module 306 may instruct the users, via the user device 103, to perform certain static posture. In one example, the data processing module 306 may instruct the users to stand-up or lay-down for a predetermined time interval (say 5 seconds). In this process, the first reference threshold value (i.e. the baseline level) for each physical activity may be determined based upon orientation information sensed by the sensors 105. In one example, the baseline level of the tilting angle 401 (shown in FIG. 4a) for a user's triceps brachia during standing may be determined as 25 degree. Further, as shown in FIG. 4b and FIG. 4c, the baseline level of a tilting angle 402 for the side thigh muscle and the back-curvature angle 403 (formed by two sensors) may be determined as 21 degree and 125 degree respectively. The baseline level determined for the tilting angle 401, the tilting angle 402 and the back-curvature angle 403, and the like may be stored with the sensor 105 itself, or the user device 103 or the data 309 within the system 101.

Figure 4D:
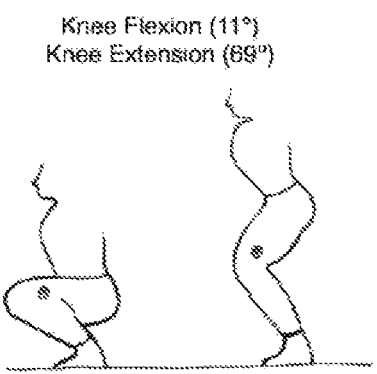
Figure 4E:
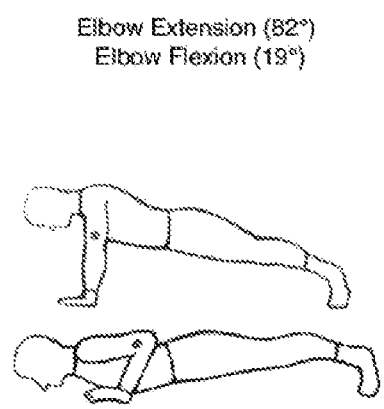
Figure 4F:
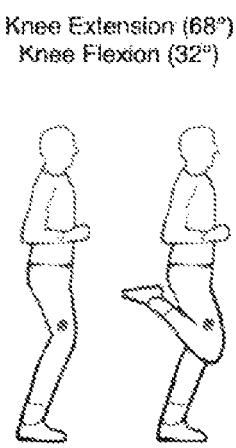

In the dynamic calibration technique, the data processing module 306 may instruct the users, via the user device 103, to perform dynamic movements including, but not limited to, squats, push up, and butt kicks for a predetermined number of times. The dynamic movements enable in determining a second reference threshold value (i.e. the minimum passing level) based on motion/orientation changes captured by the sensors 105. In one example, the user's knee angle change (58 degree) during standing squat (as shown in FIG. 4d), user's elbow angle change (63 degree) during push-up (as shown in FIG. 4e) and user's knee angle change (36 degree) during butt kicks (as shown in FIG. 4f) may be determined as the minimum passing level (i.e. the second reference threshold value) for performing/executing each of these physical activities including the squats, the push up, and the butt kicks. It must be understood that the user's knee angle change (58 degree) during standing squat is determined based on difference of an angle corresponding to knee extension (i.e. 69 degree shown in FIG. 4d) and an angle corresponding to knee flexion (i.e. 11 degree shown in FIG. 4d). Further, the user's elbow angle change (63 degree) during push-up is determined based on difference of an angle corresponding to elbow extension (i.e. 82 degree shown in FIG. 4e) and an angle corresponding to elbow flexion (i.e. 19 degree shown in FIG. 4e). Further, the user's knee angle change (36 degree) during butt kicks is determined based on difference of an angle corresponding to knee extension (i.e. 68 degree shown in FIG. 4f) and an angle corresponding to knee flexion (i.e. 32 degree shown in FIG. 4f). Similarly, the other joint angle changes sensed by the sensors 105 may be determined as the second reference threshold values.

Figure 4G:
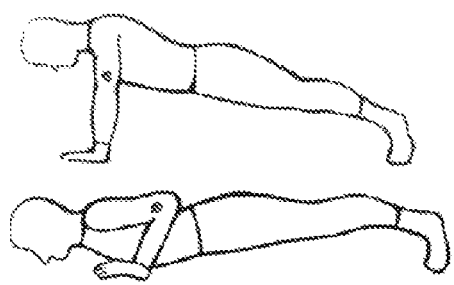
Figure 4H:
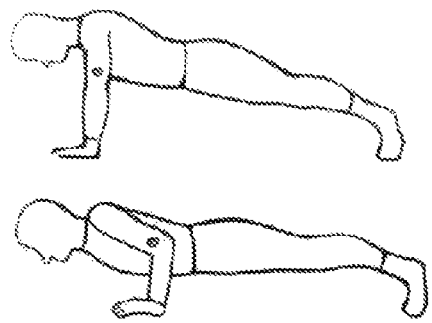

Based upon the static/dynamic calibrations, the data processing module 306 may generate a profile of the baseline levels and the minimum passing levels customized for different users depending on the posture, size and physical ability of the different users. For example, the elbow angle change determined for a skilled/advanced user is 63 degree (as shown in FIG. 4g) as against to that of 37 degree (as shown in FIG. 4h) for the intermediate user. It must be understood that the elbow angle change (i.e. 63 degree) for the skilled/advanced user is determined based on difference of an angle corresponding to elbow extension (i.e. 82 degree as shown in FIG. 4g) and an angle corresponding to elbow flexion (i.e. 19 degree as shown in FIG. 4g). Similarly, the elbow angle change (i.e. 37 degree) for the intermediate user is determined based on difference of an angle corresponding to elbow extension (i.e. 82 degree as shown in FIG. 4h) and an angle corresponding to elbow flexion (i.e. 45 degree as shown in FIG. 4h). Therefore, based upon the angle changes observed and the time spent for performing the physical activity, the data processing module 306 may generate the profile of the baseline values (i.e. the first reference threshold values) and the minimum passing level values (i.e. the second reference threshold values).

In one embodiment, after the identification of the matched motion pattern for the user, the data processing module 306 may determine a first threshold value and a second threshold value pertaining to the physical activity performed/executed by the user. Further, the data processing module 306 may compare the first threshold value and the second threshold value with the first reference threshold value and the second reference threshold value, respectively, corresponding to the matched motion pattern. It must be understood that the comparison of the threshold value and the second threshold value with the first reference threshold value and the second reference threshold value, respectively, is done in order to verify whether or not the physical activity is being performed/executed by the user in correct/effective/appropriate manner. Further, based upon the comparison, the output indication module 307 may indicate an output in form of a textual/audio/video alert to the user, wherein the output is indicative of the performance of the user in the execution of the physical activity.

In one embodiment, the data processing module 306 may enable in determining the performance of the user in the execution of the physical activity based upon the calibration techniques/methodologies as described above. However, considering the different body shapes and different skill/intensity level of the users in executing the same sports/exercises, the output indicated to the user may not be accurate. For example, even though two users are performing the same sports, the users' different body shapes and performances will result in various limb angles and acceleration data, etc. Specifically, it must be noted that though the above calibration technique determines the performance of the physical activity based upon the threshold values (e.g. baseline value and minimum passing level value), however, the above calibration technique may be chaotic in analyzing borderline scenarios wherein it is difficult to determine whether or not the particular activity, based on the threshold values, is performed correctly/incorrectly. Thus, the system need to identify tolerance level with respect to the baseline and the minimum passing levels pertaining to different physical activities such that the performance of the user is determined accurately. Therefore, in order to improve the accuracy of the output, the data processing module 306 may employ fuzzification technique explained in details as below. The purpose of implementing the fuzzification technique is to fuzzify the sensor data (especially in case of borderline scenarios) in order to increase the range of tolerance for the performance results while monitoring motion and orientation pattern of the users.

It must be understood that the performance of the user in executing the physical activity may be appropriately determined based upon user's input (initial state) and the sensor's analysis. In addition to the calibration methodology described above, the users may be divided into groups based on the difference of BMI (body mass index), age, location, intensity level or physical ability, etc. which may be entered by the users in form of users' input. Therefore, the data processing module 306 may establish a preliminary range of tolerance of physical training during the initial state. In one example, the range of tolerance of the leg angle for the squat's correct position is dependent on the intensity level of performing the squat. The higher the intensity level, the smaller the tolerance is allowed. Further, the historical sensor data captured during the training of the users may be transferred to the system and analyzed to set a range of tolerance and parameters for the equations predefined for angular fuzzification as explained in detail referring to FIG. 5 as below.

Figure 5:
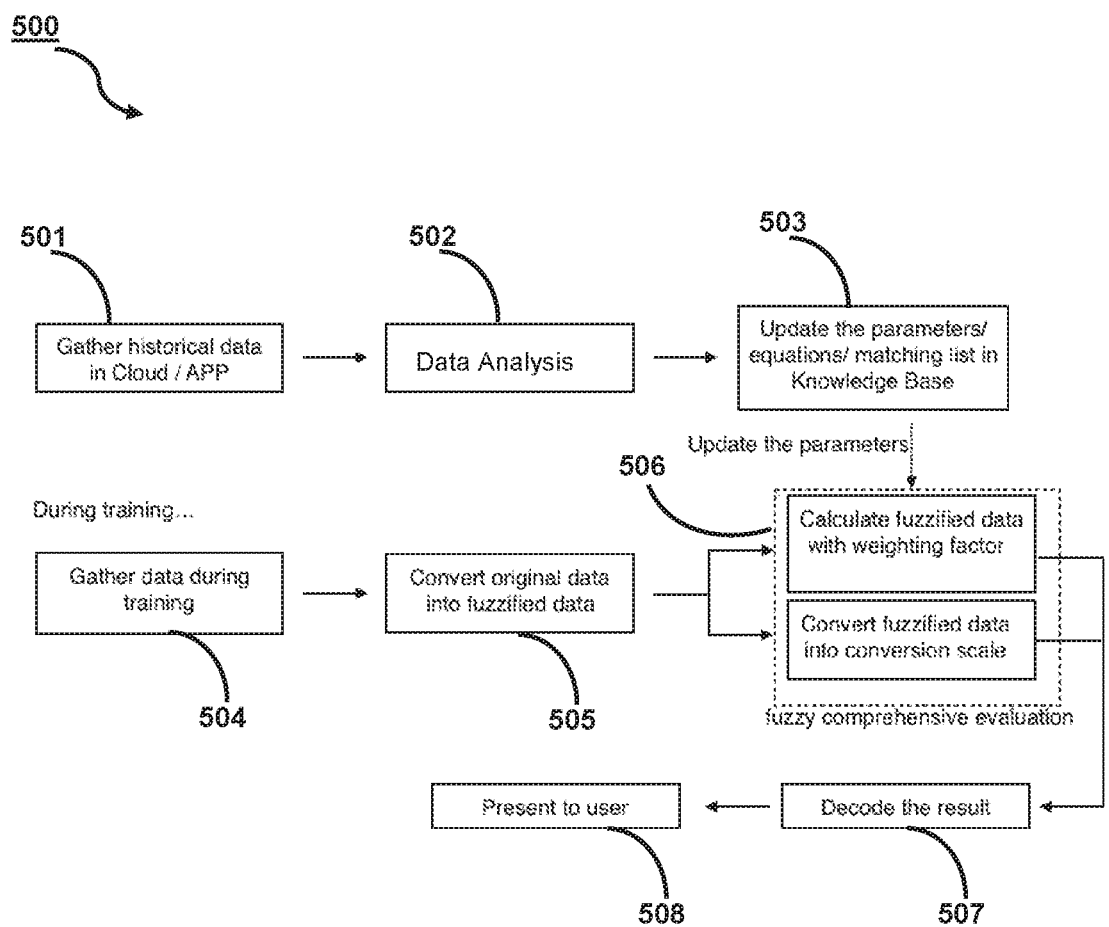
FIG. 5 illustrates a flow diagram 500 depicting the working of data processing module within the system 101, in accordance with an embodiment of the present application.

Referring to FIG. 5 is a flow diagram the working of the data processing module 306 in implementing the fuzzification technique in order to determine the performance of the user, in accordance with an embodiment of the present application. The fuzzification technique may be implemented based upon analysis of historical data captured pertaining to a plurality of users. As shown in FIG. 5, at block 501, the historical data comprising at least the motion and orientation data) associated to the physical activities executed by the users may be captured by the data capturing module 305 of the system 101. At block 502, the data processing module 306 may process the data and divide the users into groups based upon the calibrations and the user's input such as age, location and physical ability/intensity level of the user. The initial position may be defined as the baseline level which may vary with the difference in nature of sports.

Now, during the training event, if the data achieved is beyond the baseline, the sensor may record the data. The data capturing module 305 may capture the data recorded during the training event and transmit the data to the system 101 (acting as a cloud server). In one example, for the physical training such as deep squat, the maximum degree of joint angle that users perform would illustrate a curve similar to normal distribution. It must be understood that the data in form of waveform may be analyzed (at block 502) based on characteristics of sports/exercises for which a physical activity is being performed by the users. The objective of the analysis is to monitor physical capabilities of the users and recommend customized training for the users. One more input parameters (acting as a building block for the waveform) may include motion data, angular velocity, linear acceleration, gravitational direction, magnetic force, and the like. The data processing module 306 may detect distinctive elements in the waveform including amplitude, duration, scope, and the like and compare the distinctive elements with the corresponding elements of the respective sport/exercise within the knowledge base 310. Based upon the comparison, the data processing module 306 may verify whether or not the characteristics of the waveform are matching with the predefined characteristics/parameters set for the corresponding sport/exercise in the knowledge base 310. If characteristics of the waveform are matched with the predefined characteristics, the data processing module 306 may determine that the user has performed the physical activity correctly for the specific sport/exercise. Further, since the users' may improve/advance their physical conditions and skills in performing the physical activities, the predefined characteristics/parameters pertaining to the respective sports/exercise in the knowledge base 310 (and thereby the knowledge base 310 itself) may be continuously updated with the capturing of the data in form of waveforms (at block 501) and analysis of said waveforms (at block 502) at regular time intervals.

In one embodiment, the knowledge base 310 may comprise a plurality of rules indicating the performance results of the physical activities being performed, wherein the plurality of rules is derived based on historical data and expert information received from multiple experts in the physical activities of respective sports and/or exercises. In one example, the knowledge base 310 may comprise a rule derived based on expert information received from a sport coach, wherein the rule indicates whether or not a particular motion and/or orientation associated to a particular sport is performed correctly by the user. The rules may be linked with respect to the sensor data (in form of waveform as described above) captured via sensors 105 in order to determine whether or not the activities being performed by the users is correct/incorrect based upon analysis of the sensor data and the rules.

The data analyzed is stored in the knowledge base 310 (shown in FIG. 3). As shown in block 503, the data stored in the knowledge base 310 comprises essential information for adjusting the parameters for the angular fuzzification. One skilled in art would easily realize and appreciate that, the fuzzification involves converting actual data into fuzzified data based upon fuzzification rules and thereafter converting the fuzzified data into human readable format based upon de-fuzzification rules. The rules stored in the knowledge base 310 include both the fuzzification rules and the de-fuzzification rules. The fuzzification rules enables in converting the actual sensor data, captured via the sensors 105, into fuzzified data, whereas the de-fuzzification rules enables obtaining the de-fuzzified data indicative of the correct/incorrect performance of the physical activities by the users. In some embodiments, the fuzzification rules and the de-fuzzification rules are derived and continuously updated based upon analysis of the historical sensor data and expert information received from the expertise/skilled personals in the respective sports/exercises for which the physical activities of the user are being monitored. It must be understood that the knowledge base 310 may act as the internal processing centre located within the system 101 (as shown in FIG. 3) or the user device 103 itself. The knowledge base 310 may comprise details of conversion of the actual data into fuzzified data. The knowledge base 310 may comprise a predefined mapping of the fuzzified data into a predefined output (i.e. a conversion scale). The knowledge base 310 further comprises a weighting factor for each sensor and a comprehensive coefficient. It is to be noted herein that the knowledge base 310 is built and further updated based on analysis of the multiple users' training data and results thereof and cross-referencing the user's data within the groups. The knowledge base 310 along with the parameters, the matching list, the weighting factor and the comprehensive coefficient may be updated after a predefined time interval based upon addition of new training data and the results observed therefor. The knowledge base 310 may further be utilized for implementing the fuzzification technique in order to determine the performance of real time training data captured from the user.

Figure 6:
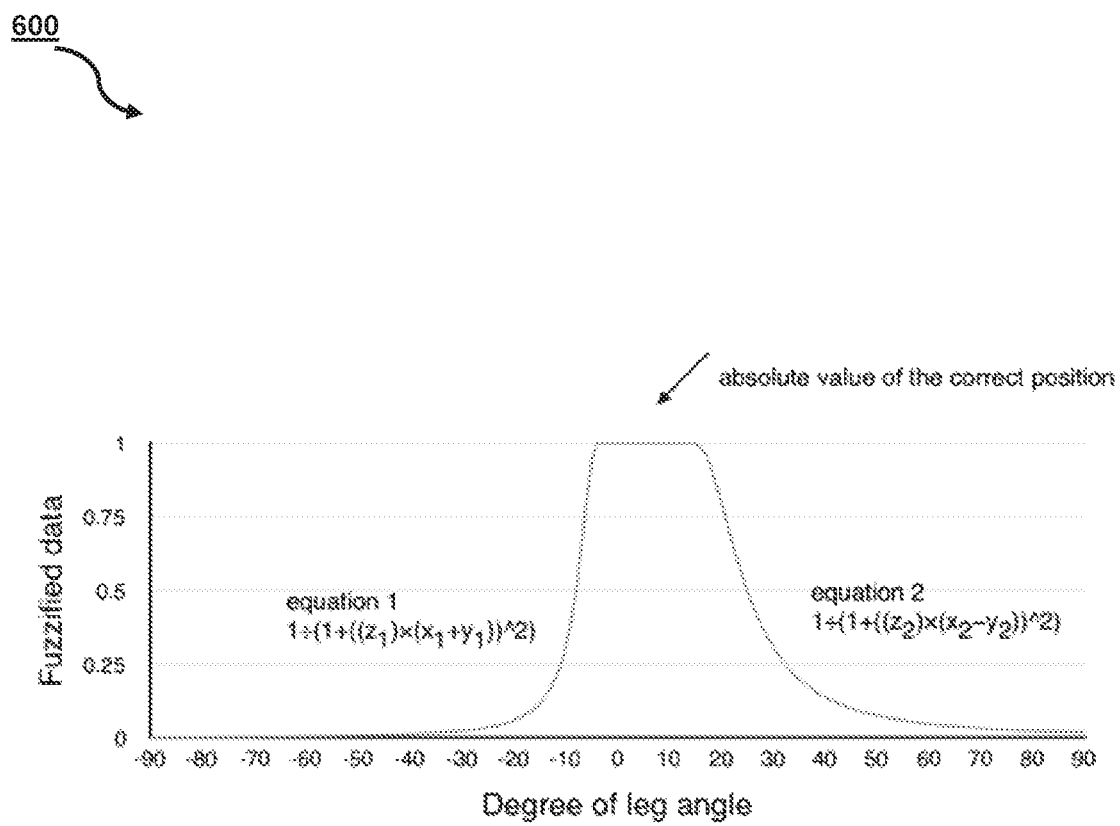
FIG. 6 illustrates a chart 600 depicting conversion of the sensor data into fuzzified data, in accordance with an embodiment of the present application.

As shown in FIG. 5, at block 504, the data processing module 306 may receive the real-time sensor data during training from the sensors 105 via the data capturing module 305. At block 505, the real-time sensor data may be converted into fuzzified data using the knowledge base 310. FIG. 6 illustrates a graph depicting the conversion of the leg angle (in degrees) into the fuzzified data having value within a range of 0-1. The graph is similar to a normal distribution curve. The fuzzified values corresponding to different values of leg angles are determined based upon fuzzification equations (1) and (2) as below:

$$1 \div (1+((z1) \times (x1+y1))^2) \quad (1)$$

$$1 \div (1+((z2) \times (x2-y2))^2) \quad (2)$$

It must be noted that the parameters of the equations may be changed/varied. The value of the parameters may be default at the initial state and may be updated from the knowledge base 310. As shown in FIG. 6, the absolute value of correct position (fuzzified data=1) is in between the equations (1) and (2). Therefore, it may be concluded that the higher the fuzzified data, the more appropriate/correct is the position of the leg angle.

Now referring to FIG. 5, at block 506, the fuzzified data may be converted into the conversion scale using the information stored in the knowledge base. It must be understood that such information facilitating the conversion may be preconfigured based on experts' input. The conversion scale enables comprehensive evaluation of fuzzified data. In one example, the conversion scale for the fuzzified data obtained in FIG. 6 is shown in below table 1.

TABLE 1

Mapping of Fuzzified data into conversion scale

| Fuzzified data | Conversion Scale |
|---|---|
| 1 | Absolutely Correct (AC) |
| 0.99~0.7 | Correct (C) |
| 0.69~0.5 | Neutral (N) |
| 0.49~0.3 | Wrong (W) |
| 0.29~0 | Absolutely Wrong (AW) |

Further, the conversion scales of different sensors may be paired using a matching list preconfigured in the knowledge base 310. In one example, for monitoring PLANK pattern, consider there are five sensors, out of which four are located in four limbs and one in lumbar region. The sensor located in the lumber region is most significant and hence considered as the primary sensor. The other four sensors are secondary sensors. The conversion scales of the primary sensor and the secondary sensors is paired using the below matching list (depicted in Table 2), in accordance with an embodiment of the present application.

TABLE 2

Matching list for pairing the conversion scales of multiple sensors

| Primary Sensor | Secondary Sensor | Final Result (based on matching list) |
|---|---|---|
| Absolutely Correct (AC) | Correct (C) | Correct |
| Correct (C) | Neutral (N) | Correct |
| Correct (C) | Correct (C) | Correct |
| Correct (C) | Absolutely Wrong (AW) | Wrong |
| Neutral (N) | Wrong (W) | Wrong |
| Absolutely Wrong (AW) | Absolutely Correct (AC) | Wrong |
| ... | ... | ... |

In another embodiment, the comprehensive evaluation of the user is based on the fuzzified data, the weighting factor of each sensor and the comprehensive coefficient. It is to be noted that the different sensors have different weighting factor which is determined based on at least the location of the sensor and the nature of the sport. In the same PLANK example as discussed above, since the primary sensor is of more significance, the weighting factor of the primary sensor is higher than the secondary sensor. In this example, consider the weighting factor of the primary sensor is 70% and the remaining four sensors is collectively 30%. In this embodiment, the fuzzy comprehensive evaluation result indicating the performance of the user in executing the activity may be determined based on equation (3) as below:

((lumber's fuzzified data×70%)+(Four
limbs'fuzzified data×30%))×comprehensive
coefficient=Fuzzy comprehensive evaluation
result     (3)

It is to be noted that the fuzzy comprehensive evaluation result obtained using equation 3 is similar to fuzzified data (i.e. within 0-1) as illustrated in Table 1. The fuzzy comprehensive evaluation result may therefore be converted into the conversion scale value as illustrated in Table 1.

As described above, the values of the comprehensive coefficient, the weighting factor of each sensor and the fuzzification of the actual sensor data may be updated from the knowledge base 310. Therefore, the data processing module 306 may enable in determining the performance of the user in the execution of the physical activity based upon the fuzzification technique described above. The output indication module 307 may indicate the performance of the user in executing the physical activity via a notification alert on the user device 103. Specifically, based upon the final results as depicted in the table above, the output indication module 307 may notify the user, via the user device 103, the output in form of a textual/audio/visual message indicating the performance of the user in executing the physical activity. In one example, the message may be RIGHT/CORRECT or WRONG/INCORRECT based upon the results obtained from the Table 1 and Table 2 above. Further, the output indication module 307 may recommend one or more customized trainings to the user based upon the performance of the user.

Figure 7:
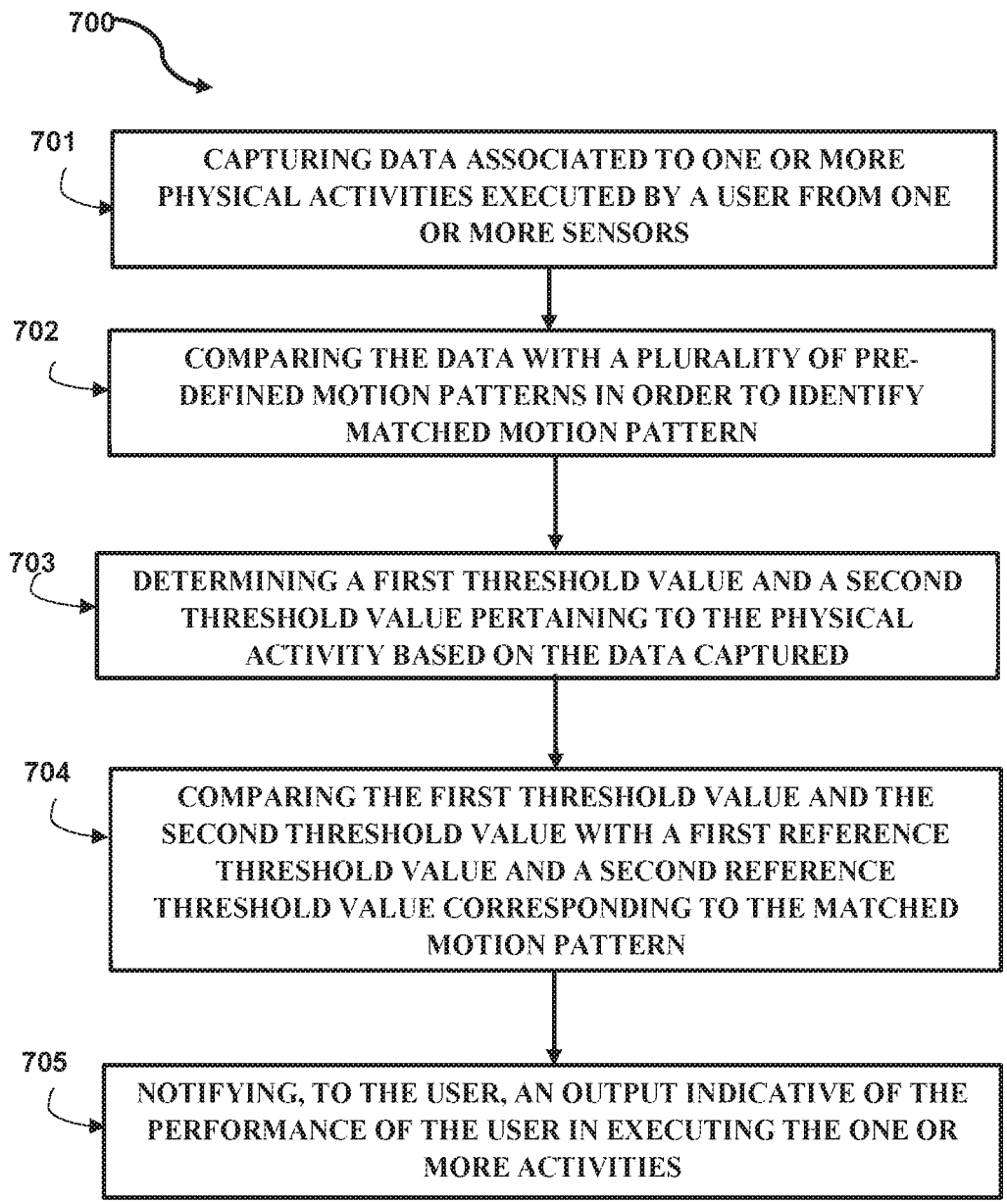
FIG. 7 illustrates a method 700 for monitoring motion and orientation patterns associated to one or more physical activities of a user, in accordance with the embodiment of the present subject matter.

Referring now to FIG. 7, a method 700 for monitoring motion and orientation patterns associated to one or more physical activities of a user to the user is shown, in accordance with an embodiment of the present subject matter. The order in which the method 700 is described is not intended to be construed as a limitation, and any number of the described method blocks can be combined in any order to implement the method 700 or alternate methods. Furthermore, the method 700 can be implemented in any suitable hardware, software, firmware, or combination thereof. However, for ease of explanation, in the embodiments described below, the method 700 may be considered to be implemented in the above described system 101.

At block 701, data associated to one or more physical activities executed by a user may be captured. The data may be captured from the sensors 105. The data may include at least motion and orientation data of the user while executing the physical activities. In one implementation, the data may be captured from the sensors 105 via the data capturing module 305 of the system 101. The data may be stored in the data 309 of the system 101.

At block 702, the data captured may be compared with a plurality of pre-defined motion patterns in order to identify a matched motion pattern. In one aspect, each pre-defined motion pattern comprises a first reference threshold value and a second reference threshold value, wherein the first reference threshold value and the second reference threshold value indicates a baseline level and a minimum passing level, respectively, required for the successful execution of the one or more physical activities. In one implementation, the data captured may be compared with the plurality of pre-defined motion patterns to identify the matched motion pattern by the data processing module 306.

At block 703, a first threshold value and a second threshold value pertaining to the one or more physical activities executed by the user may be determined based upon the data captured. In one implementation, the first threshold value and the second threshold value may be determined by the data processing module 306.

At block 704, the first threshold value and the second threshold value may be compared with the first reference threshold value and the second reference threshold value, respectively, corresponding to the matched motion pattern. In one implementation, the first threshold value and the second threshold value may be compared with the first reference threshold value and the second reference threshold value by the data processing module 306.

At block 705, the user, based upon the comparison, may be notified with an output indicative of the performance of the user in executing the one or more activities. In one implementation, the user may be notified with an output by the output indication module 307.

Although implementations for methods and systems for monitoring motion and orientation patterns associated to one or more physical activities of a user have been described in language specific to structural features and/or methods, it is to be understood that the appended claims are not necessarily limited to the specific features or methods described. Rather, the specific features and methods are disclosed as examples of implementations for monitoring motion and orientation patterns associated to one or more physical activities of a user.

What is claimed is:

1. A system for monitoring motion and orientation patterns associated to one or more physical activities of a user, the system comprising:
   one or more sensors, wherein the one or more sensors are positioned within an upper garment and a lower garment of the user;
   a processor in communication with the one or more sensors;
   a memory coupled with the processor, wherein the processor executes programmed instructions stored in the memory for:
      capturing data associated to one or more physical activities executed by a user from the one or more sensors, wherein the physical activities comprise a static posture and one or more dynamic movements, wherein the data comprises at least motion and orientation data, wherein the motion and the orientation data include a tilting angle, a curvature angle, an extension angle, and a flexion angle;
      comparing the data with a plurality of pre-defined motion patterns in order to identify a matched motion pattern, wherein each pre-defined motion pattern comprises a first reference threshold value and a second reference threshold value, wherein the first reference threshold value and the second reference threshold value indicates a baseline level and a minimum passing level, respectively, required for a successful execution of the one or more physical activities, wherein the baseline level and the minimum passing level is determined based upon static and dynamic calibration techniques respectively, wherein the static calibration technique is used when the user is instructed to perform the static posture and the dynamic calibration technique is used when the user is instructed to perform the dynamic movements, wherein the static and/or dynamic calibration techniques enable in generating a profile of baseline levels and minimum passing levels customized for different users depending on posture, size and physical ability of the different users;
      determining, based upon the data, a first threshold value and a second threshold value pertaining to the one or more physical activities executed by the user;
      comparing the first threshold value and the second threshold value with the first reference threshold value and the second reference threshold value, respectively, corresponding to the matched motion pattern; and notifying an output to the user based upon the comparison of the first threshold value and the second threshold value with the first reference threshold value and the second reference threshold value, wherein the output is indicative of a performance of the user in executing the one or more physical activities;

wherein the data captured from the one or more sensors is converted into a fuzzified data using a knowledge base.

2. The system of claim 1, wherein the knowledge base further comprises predefined mapping of the fuzzified data with historical data captured from the one or more sensors, wherein the historical data is associated to a plurality of users categorized into a plurality of groups.

3. The system of claim 2, wherein the plurality of users is categorized into the plurality of groups based upon age, Body-Mass Index (BMI), physical ability, location and a combination thereof.

4. The system of claim 3, wherein the knowledge base further comprises one or more parameters enabling the conversion of the data into the fuzzified data, wherein the one or more parameters are derived based upon an analysis of the historical data, and wherein the one or more parameters comprises at least a group category, a type of a physical activity, and an intensity level of the physical activity.

5. The system of claim 4, wherein the knowledge base further comprises a predefined mapping of the fuzzified data to a predefined output, the predefined output indicating the performance of the users in executing the one or more physical activities.

6. The system of claim 5, wherein the output notified to the user is based upon a plurality of factors comprising one or more of weighting factor of the one or more sensors, the fuzzified data corresponding to the data captured by the one or more sensors and a coefficient.

7. The system of claim 6, wherein the weighting factor and the coefficient are derived based upon analysis of the historical data within the knowledge base.

8. The system of claim 7, wherein the weighting factor is derived based upon at least a location of the one or more sensors and a type of a physical activity being executed by the users.

9. The system of claim 8, wherein the knowledge base is frequently updated after a predefined time interval, and wherein the updating of the knowledge base comprises updating of the one or more parameters enabling the conversion of the data into the fuzzified data, the predefined mapping of the fuzzified data to a predefined output, the weighting factor of the one or more sensors and the coefficient.

10. A method for monitoring motion and orientation patterns associated to one or more physical activities of a user, the method comprising:

capturing, by a processor, data associated to one or more physical activities executed by a user from one or more sensors, wherein the one or more sensors are positioned within an upper garment and a lower garment of the user, wherein the physical activities comprise a static posture and one or more dynamic movements, wherein the data comprises at least motion and orientation data, wherein the motion and the orientation data include a tilting angle, a curvature angle, an extension angle, and a flexion angle;

comparing, by the processor, the data with a plurality of pre-defined motion patterns in order to identify a matched motion pattern, wherein each pre-defined motion pattern comprises a first reference threshold value and a second reference threshold value, wherein the first reference threshold value and the second reference threshold value indicates a baseline level and a minimum passing level, respectively, required for a successful execution of the one or more physical activities, wherein the baseline level and the minimum passing level is determined based upon static and dynamic calibration techniques respectively, wherein the static calibration technique is used when the user is instructed to perform the static posture and the dynamic calibration technique is used when the user is instructed to perform the dynamic movements, wherein the static and/or dynamic calibration techniques enable in generating a profile of baseline levels and minimum passing levels customized for different users depending on posture, size and physical ability of the different users;

determining, by the processor, based upon the data, a first threshold value and a second threshold value pertaining to the one or more physical activities executed by the user;

comparing, by the processor, the first threshold value and the second threshold value with the first reference threshold value and the second reference threshold value, respectively, corresponding to the matched motion pattern; and notifying an output to the user based upon the comparison of the first threshold value and the second threshold value with the first reference threshold value and the second reference threshold value, wherein the output is indicative of a performance of the user in executing the one or more activities;

wherein the method further comprises: converting, by the processor, the data captured from the one or more sensors into a fuzzified data using a knowledge base.

11. The method of claim 10, wherein the knowledge base further comprises a predefined mapping of the fuzzified data with historical data captured from the one or more sensors, wherein the historical data is associated to a plurality of users categorized into a plurality of groups.

12. The method of claim 11 further comprising deriving, by the processor, one or more parameters based upon an analysis of the historical data, wherein the one or more parameters enable in the conversion of the data into the fuzzified data, and wherein the one or more parameters comprises at least a group category, a type of a physical activity, and an intensity level of the physical activity.

13. The method of claim 12, wherein the knowledge base further comprises a predefined mapping of the fuzzified data to a predefined output, the predefined output indicating the performance of the users in executing the one or more activities.

14. The method of claim 13, wherein the output notified to the user is based upon a plurality of factors comprising one or more of weighting factor of the one or more sensors, the fuzzified data corresponding to the data captured by the one or more sensors and a coefficient.

15. The method of claim 14 further comprising deriving, by the processor, the weighting factor and the coefficient based upon analysis of the historical data within the knowledge base, and wherein the weighting factor is derived based upon at least a location of the one or more sensors and a type of a physical activity being executed by the users.

16. The method of claim 15 further comprises frequently updating, by the processor, the knowledge base after a predefined time interval, wherein the updating of the knowledge base further comprises updating of the one or more parameters enabling the conversion of the data into the fuzzified data, the predefined mapping of the fuzzified data to a predefined output, the weighting factor of the one or more sensors and the coefficient.

17. A non-transitory computer readable medium storing program for monitoring motion and orientation patterns associated to one or more physical activities of a user, the program comprising programmed instructions for:

capturing data associated to one or more physical activities executed by a user from one or more sensors, wherein the one or more sensors are positioned within an upper garment and a lower garment of the user, wherein the physical activities comprise a static posture and one or more dynamic movements, wherein the data comprises at least motion and orientation data, wherein the motion and the orientation data include a tilting angle, a curvature angle, an extension angle, and a flexion angle;

comparing the data with a plurality of pre-defined motion patterns in order to identify a matched motion pattern, wherein each pre-defined motion pattern comprises a first reference threshold value and a second reference threshold value, wherein the first reference threshold value and the second reference threshold value indicates a baseline level and a minimum passing level, respectively, required for a successful execution of the one or more physical activities, wherein the baseline level and the minimum passing level is determined based upon static and dynamic calibration techniques respectively, wherein the static calibration technique is used when the user is instructed to perform the static posture and the dynamic calibration technique is used when the user is instructed to perform the dynamic movements, wherein the static and/or dynamic calibration techniques enable in generating a profile of baseline levels and minimum passing levels customized for different users depending on posture, size and physical ability of the different users;

determining, based upon the data, a first threshold value and a second threshold value pertaining to the one or more physical activities executed by the user;

comparing the first threshold value and the second threshold value with the first reference threshold value and the second reference threshold value, respectively, corresponding to the matched motion pattern; and notifying an output to the user based upon the comparison of the first threshold value and the second threshold value with the first reference threshold value and the second reference threshold value, wherein the output is indicative of a performance of the user in executing the one or more physical activities;

wherein the data captured from the one or more sensors is converted into a fuzzified data using a knowledge base.

\* \* \* \* \*